United States Patent [19]
Khambay et al.

[11] Patent Number: 5,763,700
[45] Date of Patent: Jun. 9, 1998

[54] PESTICIDAL FLUOROOLEFINS

[75] Inventors: Bhupinder Pall Singh Khambay, Southall; Mu-Guang Liu, Fallowfield, both of England

[73] Assignee: British Technology Group Limited, Londin, England

[21] Appl. No.: 403,795

[22] PCT Filed: Sep. 16, 1993

[86] PCT No.: PCT/GB93/01959

§ 371 Date: Mar. 16, 1995

§ 102(e) Date: Mar. 16, 1995

[87] PCT Pub. No.: WO94/06741

PCT Pub. Date: Mar. 31, 1994

[30] Foreign Application Priority Data

Sep. 16, 1992 [GB] United Kingdom ............ 9219612

[51] Int. Cl.$^6$ ........................................ C07C 22/04
[52] U.S. Cl. ................... 570/128; 570/143; 570/133; 568/631; 568/633; 568/634; 585/20; 585/25
[58] Field of Search ................... 568/631, 633, 568/634; 570/128, 143; 585/20, 25

[56] References Cited

FOREIGN PATENT DOCUMENTS

| | | |
|---|---|---|
| 0094085 | 11/1983 | European Pat. Off. . |
| 0104908 | 4/1984 | European Pat. Off. . |
| 0125204 | 11/1984 | European Pat. Off. . |
| 0136451 | 4/1985 | European Pat. Off. . |
| 0198791 | 10/1986 | European Pat. Off. . |
| 8504651 | 10/1985 | WIPO . |
| 8601501 | 3/1986 | WIPO . |

*Primary Examiner*—Gary Geist
*Assistant Examiner*—Rosalynd Keys
*Attorney, Agent, or Firm*—Graham & James LLP

[57] ABSTRACT

A pesticidal compound, suitable for combating soil borne insect pests has formula I:

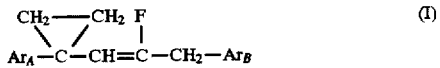

in which formula:

$Ar_A$ represents a phenyl or naphthyl group optionally substituted by one or more groups selected from halogen, alkoxy, haloalkoxy, methylenedioxy, $C_1$–$C_6$ alkyl and $C_1$–$C_6$ haloalkyl; and $Ar_B$ represents a phenoxy, phenyl, benzyl or benzoyl-substituted phenyl group which is optionally further substituted;

the configuration of the aryl cyclopropyl group and the group $CH_2Ar_B$ about the double bond being mutually trans.

15 Claims, No Drawings

PESTICIDAL FLUOROOLEFINS

This invention relates to pesticidal compounds and is particularly concerned with soil insecticides.

There is continuing interest in the discovery of compounds which, while not necessarily having wide spectrum pesticidal activity, have high activity in a particular mode of application and/or in respect of particular pests, especially insect and similar invertebrate pests which inhabit the soil. Thus, for example, GB Patent Specification No. 2066810 describes certain fluorinated-benzyl esters of cyclopropane carboxylic acids which have, inter alia, soil insecticidal activity. However, there is little understanding in the pesticide art of the various factors which contribute and interact in order to provide compounds having good activity against soil borne pests. For good soil activity, many more factors come into play, affecting migration, persistence and transference of the active compound to the soil borne insect, than is the case when considering topical application. A review of such factors is to be found in a recent paper by Simmons et al (1992) J. Agric. Food Chem., 40, 1432–1436.

It has now been surprisingly found that good soil insecticide activity is demonstrated by a group of non-ester aryl cyclopropyl substituted olefins having a fluorine substituent at the site of olefinic unsaturation.

The present invention comprises pesticidal compounds of formula I:

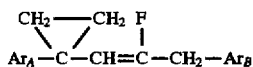

in which formula:

Ar$_A$ represents a phenyl or naphthyl group optionally substituted by one or more groups selected from halogen, alkoxy, haloalkoxy, methylenedioxy, $C_1$–$C_6$ alkyl and $C_1$–$C_6$ haloalkyl; and Ar$_B$ represents a phenoxy, phenyl, benzyl or benzoyl-substituted phenyl group which is optionally further substituted;

the configuration of the aryl cyclopropyl group and the group CH$_2$Ar$_B$ about the double bond being mutally trans.

Preferably Ar$_A$ is a substituted phenyl group. Substitution is preferably at the 3-(meta) and/or 4-(para) position by fluorine, bromine, chlorine, a $C_1$–$C_6$ alkyl group (such as methyl or t-butyl), a $C_1$–$C_6$ alkoxy group (such as methoxy or ethoxy), a $C_1$–$C_6$ haloalkoxy group comprising one or more halogens (such as —OCF$_3$ and —OCF$_2$H) or a $C_1$–$C_6$ haloalkyl group (e.g. CF$_3$). Ar$_A$ generally carries no more than two substituents.

Ar$_B$ may be considered as representing the residue of a benzyl alcohol Ar$_B$CH$_2$OH as described and claimed in UK Patent Specification No. 1413491 and which gives rise to significant insecticidal activity when esterified with [1R,cis] -2,2-dimethyl-3-(2,2-dibromovinyl) carboxylic acid. Such significant insecticidal activity is demonstrated by a potency towards houseflies of usually at least 5 relative to bioresmethrin =100.

The group Ar$_B$ may be a phenyl group substituted by phenoxy, phenyl, benzyl or benzoyl, especially at the 3-(meta) position. Additionally the phenyl group may be substituted, especially by fluorine, more especially at the 4-(para) position. 3-phenoxyphenyl and 4-fluoro-3-phenoxyphenyl groups Ar$_B$ are of particular interest.

It has been found that, although the presence of fluorine in the group Ar$_B$ may lead to enhanced activity of the compound of formula I as a soil insecticide, this is by no means a constant improvement and in many cases the activity as a soil insecticide is diminished by fluorine incorporation. In contrast, there has been found a marked and consistent improvement in soil insecticide activity of compounds of formula I, with a fluorine on an olefinic carbon, when compared with compounds of formula I lacking such a fluorine.

The compounds of this invention constitute a selection from the broad class of compounds claimed in our prior patent GB 2,167,749. The prior compounds were described as having insecticidal activity against a wide range of plant pests and as being of especial value for use against rice pests. The compounds of the present invention are therefore a group of novel compounds found to have a specific and unexpected utility as soil insecticides.

The invention further includes a process for the preparation of a pesticidal compound of formula I in which a compound comprising a moiety

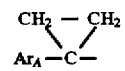

and a compound comprising a moiety Ar$_B$— are reacted together forming a link —CH=C(F)CH$_2$— between

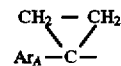

and Ar$_B$ in the compound of formula I.

A preferred process comprises the catalytic reaction of a nucleophilic species formally of formula Ar$_B$— with a compound of formula

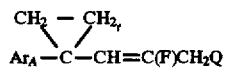

where Q represents a good leaving group.

Typically, the reaction is carried out in the presence of a transition metal catalyst, which is preferably a copper salt or a complex thereof with a lithium salt.

The nucleophilic species Ar$_B$— is generally present in the form of a Grignard reagent of formula Ar$_B$ MgBr or an alkali-metal compound, e.g. Ar$_B$ Li, and the leaving group Q is typically halogen, e.g. bromine, or acyloxy, e.g. acetoxy. The copper salt is suitably a cuprous salt, especially a halide (e.g. bromide or iodide) or cyanide. Complexes of copper of formula Li$_2$ Cu Y$_2$ Z$_2$, where Y and Z represent chlorine, bromine, iodine or cyano, may also be used as catalysts. Such transformations are described by Erdick, Tetrahedron, 1984, 40, 641–657.

The following route illustrates a typical procedure for preparation of compounds I where Q in the final step is acetoxy.

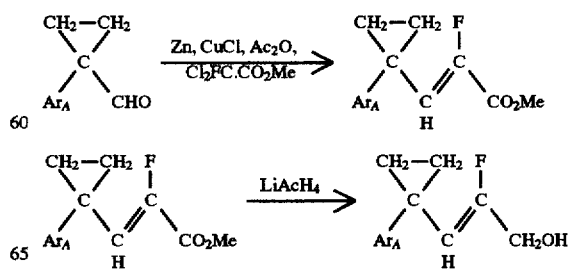

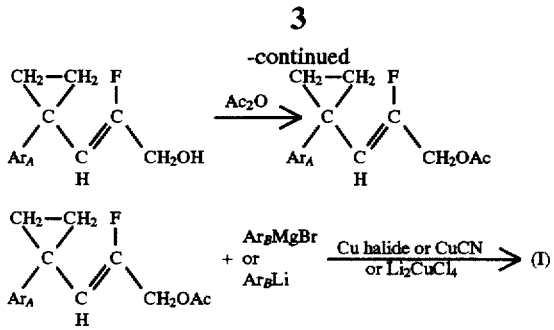

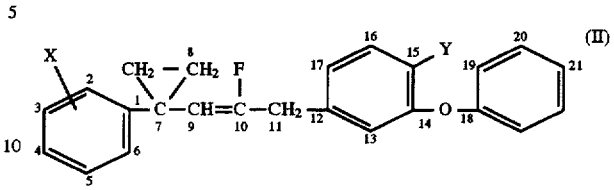

The initial step in the reaction scheme illustrated above is a type of Reformatsky reaction between dichlorofluoroacetate and the appropriate aldehyde. This method has been described for use with a variety of aliphatic and aromatic aldehydes by T. I. Shihara and M. Kuraboshi in chemistry letters 1987, 1145–1148 (The Chemical Society of Japan) the contents of which are incorporated herein by reference. The subsequent steps to convert the carbomethoxy to an acetoxy group can be carried out by using known methods. The final step of the process corresponds to that described in GB 2,167,749.

The Grignard reagents $Ar_B$ MgBr may be prepared by the methods and via the intermediates described in UK Patent Nos. 2226315 and 2187731 if desired.

As indicated above, the compounds of formula I find particular application as soil insecticides, either for soil application or as a seed treatment. The invention therefore further comprises an insecticidal composition comprising an insecticidally effective amount of a compound of formula I in association with an agriculturally acceptable diluent.

Suitable diluents for use as a soil insecticide include both solid and liquid diluents so as to provide compositions which can be formulated for example as granules, dusts or emulsifiable concentrates. Examples of diluents suitable for the preparation of granular compositions are porous materials such as pumice, gypsum or corn cob grits. Suitable diluents for the preparation of dusts include kaolin, bentonite, kieselguhr or talc. For the preparation of emulsifiable concentrates, various solvents, such as ketones and aromatic solvents, may be employed together with one or more known wetting agents, dispersing agents or emulsifying agents.

Solid compositions especially granules, preferably contain from 0.5 to 5% by weight of active ingredient, while liquid compositions, as applied to the crop, may contain as little as from 0.0001 to 1% by weight of active ingredient.

Dependent on the mode of use, the compositions may conveniently be applied to the locus of infestation at an application rate of from 1 to 100 g of active ingredient per hectare.

It will be appreciated that the compositions may include a mixture of compounds of formula I and/or other ingredients, including another pesticidal material, eg. an insecticide, acaricide or fungicide.

The compositions may be used for combating soil borne pests such as those of the orders Coleoptera, Lepidoptera and Diptera, particularly root worms, cut worms, wireworms, millipedes, and wheat bulb fly. It is intended that the compositions may be applicable to soil and/or seeds during cultivation of a wide variety of crops such as maize, sugar beet, potatoes, tobacco and cotton.

The invention will now be further described with reference to the following examples.

Examples 1 to 24 relate to the preparation of intermediates, Examples 25 to 40 to the preparation of compounds of formula I and Example 41 to the use of compounds of the invention as soil insecticides. In the Examples 25 to 40, 13 CNMR peaks are listed as assigned peaks in the order indicated by the following diagram:

Equivocal assignments are indicated by superscrips, a,b,c. Peaks not detected above the noise level are Indicated by N. Coupling constants to fluorine are given in brackets, and are in Hz. — indicates a shift already given due to symmetrical identity.

EXAMPLE 1

1-(4-Chlorophenyl)-1-(2-fluoro-2-(methoxycarbonyl) ethenyl)cyclopropane

To a stirred mixture of acid-washed zinc powder (3.33 g), copper (I) chloride (0.53 g) and molecular sieve 4A (3.6 g) in dry tetrahydrofuran (40 ml) under nitrogen, 1-(4-chlorophenyl)-1-formycyclopropane (2.96 g) was added slowly, followed by acetic anhydride (1.5 ml). After the mixture had been warmed to 50°, methyl dichlorofluoroacetate (2.73 g) was added dropwise, and stirring continued for 4 h at 50°. After cooling, the mixture was diluted with diethyl ether (150 ml), filtered through a bed of celite, and the filtrate was concentrated under reduced pressure. The residual oil was chromatographed on silica gel using diethyl ether/hexane (1:9) to yield 1-(4-chlorophenyl)-1-(2-fluoro-2-(methoxycarbonyl)ethenyl)cyclopropane (1.12 g, 27%).

EXAMPLE 2

1-(4-Ethoxyphenyl)-1-(2-fluoro-2-(methoxycarbonyl) ethenyl)cyclopropane

The method of Example 1 was repeated using zinc powder (4.1 g), copper (I) chloride (0.63 g), molecular sieve 4A (4.2 g), tetrahydrofuran (72 ml), 1-(4-ethoxyphenyl)-1-formylcyclopropane (4.7 g), acetic anhydride (2.6 ml) and methyl dichloro-fluoroacetate (3.3 g) to yield the title compound (3.4 g, 52%).

EXAMPLE 3

1-(2-Fluoro-2-(methoxycarbonyl)ethenyl)-1-(4-trifluoromethoxyphenyl)cyclopropane The method of Example 1 was repeated using zinc powder (1 g), copper (I) chloride (0.16 g), molecular sieve 4A (1.1 g), tetrahydrofuran (18 ml), 1-formyl-1-(4-trifluoromethoxyphenyl)cyclopropane (1.08 g), acetic anhydride (0.6 ml) and methyl dichlorofluoroacetate (0.86 g) to yield the title compound (0.45 g, 34%).

EXAMPLE 4

1-(2-Fluoro-2-(methoxycarbonyl)ethenyl)-1-(4-fluorophenyl)cyclopropane

The method of Example 1 was repeated using zinc powder (1 g), copper (I) chloride (0.12 g) and molecular sieve 4A (1 g), tetrahydrofuran (18 ml), 1-(4-fluorophenyl)-1-formyl-cyclopropane (0.54 g), acetic anhydride (0.38 ml) and methyl dichlorofluoroacetate (0.69 g) to yield the title compound (0.32 g, 42%).

EXAMPLE 5

1-(2-Fluoro-2-(methoxycarbonyl)ethenyl)-1-(2-fluoro-4-trifluoromethylphenyl) cyclopropane The method of Example 1 was repeated using zinc powder (1.3 g), copper (I) chloride (0.22 g), molecular sieve 4A (1.6 g), tetrahydrofuran (20 ml), 1-(2-fluoro-4-trifluoromethylphenyl)-1-formylcyclopropane (1.39 g), acetic anhydride (0.58 ml) and methyl dichlorofluoroacetate to yield the title compound (0.81 g, 44%).

EXAMPLE 6

1-(2-Fluoro-2-(methoxycarbonyl)ethenyl)-1-(3,4-methylenedioxyphenyl)cyclopropane The method of Example 1 was repeated using zinc powder (2.94 g), copper (I) chloride (0.45 g) molecular sieve 4A (3 g), tetrahydrofuran (54 ml), 1-formyl-1-(3,4-methylenedioxyphenyl)cyclopropane (3.09 g), acetic anhydride (1.5 ml) and methyl dichlorofluoroacetate (2.36 g) to yield the title compound (2.2 g, 51%).

EXAMPLE 7

1-(2,4-Difluorophenyl)-1-(2-fluoro-2(methoxycarbonyl)ethenyl)cyclopropane

The method of Example 1 was repeated using zinc powder (1 g), copper (I) chloride (0.12 g), molecular sieve 4A (1 g), tetrahydrofuran (18 ml), 1-(2,4-difluorophenyl)-1-formylcyclopropane (0.44 g), acetic anhydride (0.4 ml) and methyl dichlorofluoroacetate (0.62 g) to yield the title compound (0.24 g, 39%).

EXAMPLE 8

1-(4-Difluoromethoxyphenyl)-1-(2-fluoro-2(methoxycarbonyl)ethenyl)cyclopropane

The method of Example 1 was repeated using zinc powder (2.8 g), copper (I) chloride (0.42 g), molecular sieve 4A (2.8 g) tetrahydrofuran (50 ml), 1-(4-difluoromethoxyphenyl)-1-formylcyclopropane, acetic anhydride (1.5 ml) and methyl dichlorofluoroacetate (3.6 g) to yield the title compound (0.79 g, 28%).

EXAMPLE 9

1-(4-Chlorophenyl)-1-(2-fluoro-3-hydroxyprop-1-enyl)cyclopropane 1-(4-Chlorophenyl)-1-(2-fluoro-2-(methoxycarbonyl)ethenyl)cyclopropane prepared as described In Example 1 (0.73 g) in dry diethyl ether (10 ml) was added dropwise to a stirred suspension of lithium aluminium hydride (0.18 g) in dry diethyl ether at 0° C. Stirring was continued during 40 min, while the mixture warmed to room temperature. Water (20 ml) was added, and the mixture was extracted with diethyl ether (3×20 ml). The combined organic layers were washed with water (3×10 ml), dried and evaporated under reduced pressure. The residue was chromatographed on silica using diethyl ether/hexane (1:2) to yield 1-(4-chlorophenyl)-1-(2-fluoro-3-hydroxyprop-1-enyl) cyclopropane (0.56 g, 86%).

EXAMPLE 10

1-(4-Ethoxyphenyl)-1-(2-fluoro-3-hydroxyprop-1-enyl) cyclopropane

The method of Example 9 was repeated using 1-(4-ethoxyphenyl)-1-(2-fluoro-2-(methoxycarbonyl)ethenyl)cyclopropane (Example 2) (2.3 g), diethyl ether (20 ml) and lithium aluminium hydride (0.55 g) to yield the title compound (1.51 g, 74%).

EXAMPLE 11

1-(2-Fluoro-3-hydroxyprop-1-enyl)-1-(4-trifluoromethoxyphenyl)cyclopropane

The method of Example 9 was repeated using 1-(2-fluoro-2-(methoxycarbonyl)ethenyl)1-(4-trifluoromethoxyphenyl) cyclopropane (Example 3) (0.39 g), diethyl ether (10 ml) and lithium aluminium hydride (0.11 g) to yield the title compound (0.28 g, 80%).

EXAMPLE 12

1-(2-Fluoro-3-hydroxyprop-1-enyl)-1-(4-fluorophenyl) cyclopropane

The method of Example 9 was repeated using 1-(2-fluoro-2-(methoxycarbonyl)ethenyl)-1-(4-fluorophenyl)-cyclopropane (Example 4) (0.29 g), diethyl ether (10 ml) and lithium aluminium hydride (0.11 g) to yield the title compound (0.23 g, 91%).

EXAMPLE 13

1-(2-fluoro-3-hydroxyprop-1-enyl)-1-(2-fluoro-4-trifluoromethylphenyl)cyclopropane The method of Example 9 was repeated using 1-(2-Fluoro-2-(methoxycarbonyl)ethenyl)-1-(2-fluoro-4-trifluoromethylphenyl)-cyclopropane (Example 5) (0.77 g), diethyl ether (10 ml) and lithium aluminium hydride (0.18 g) to yield the title compound (0.54 g, 77%).

EXAMPLE 14

1-(2-fluoro-3-hydroxyprop-1-enyl)-1-(3,4-methylenedioxyphenyl)cyclopropane

The method of Example 9 was repeated using 1-(2-Fluoro-2-(methoxy-carbonyl)ethenyl)-1-(3,4-methylenedioxyphenyl)cyclopropane (Example 6) (0.98 g), diethyl ether (15 ml) and lithium aluminium hydride (0.37 g) to yield the title compound (0.78 g, 88%).

EXAMPLE 15

1-(2,4-Difluorophenyl)-1-(2-fluoro-3-hydroxyprop-1-enyl) cyclopropane

The method of Example 9 was repeated using 1-(2,4-difluorophenyl)-1-(2-fluoro-2(methoxycarbonyl)ethenyl) cyclopropane (Example 7) (0.37 g), diethyl ether (10 ml) and lithium aluminium hydride (0.14 g) to yield the title compound (0.23 g, 71%).

EXAMPLE 16

1-(4-Difluoromethoxyphenyl)-1-(2-fluoro-3-hydroxyprop-1-enyl)cyclopropane

The method of Example 9 was repeated using 1-(4-difluoromethoxyphenyl)-1-(2-fluoro-2(methoxycarbonyl)-ethenyl)cyclopropane (Example 8) (0.77 g), diethyl ether (10 ml) and lithium aluminium hydride (0.2 g) to yield the title compound (0.63 g, 89%).

EXAMPLE 17

1-(3-Acetoxy-2-fluoroprop-1-enyl)-1-(4-chlorophenyl) cyclopropane

Acetyl chloride (0.72 ml) was slowly added to a stirred solution of 1-(4-chlorophenyl)-1-(2-fluoro-3-hydroxyprop-1-enyl)cyclopropane (Example 9) (0.36 g) in benzene (20 ml) and pyridine (0.14 ml) at 0° C., and stirring was continued for 24 h while the mixture warmed to room temperature. After addition of water (10 ml), the mixture was extracted with diethyl ether (3×20 ml) and the combined organic layers were washed with water (3×10 ml) and evaporated under reduced pressure. The residue was chromatographed on silica using diethyl ether/hexane (1:9) to yield 1-(3-acetoxy-2-fluoroprop-1-enyl)-1-(4-chlorophenyl) cyclopropane (0.37 g, 87%).

EXAMPLE 18

1-(3-Acetoxy-2-fluoroprop-1-enyl)-1-(4-ethoxyphenyl) cyclopropane

The method of Example 17 was repeated using acetyl chloride (2 ml), 1-(4-ethoxyphenyl)-1-(2-fluoro-3-hydroxyprop-1-enyl)cyclopropane (Example 10) (0.99 g), benzene (50 ml) and pyridine (0.38 ml) to yield the title compound (1.16 g, 99%).

EXAMPLE 19
1-(3-Acetoxy-2-fluoroprop-1-enyl)-1-(4-trifluoromethoxyphenyl)cyclopropane The method of Example 17 was repeated using acetyl chloride (0.46 ml), 1-(2-fluoro-3-hydroxyprop-1-enyl)-1-(4-trifluoromethoxy-phenyl)cyclopropane (Example 11) (0.25 g), benzene (12 ml) and pyridine (0.09 ml) to yield the title compound (0.27 g, 92%).

EXAMPLE 20
1-(3-Acetoxy-2-fluoroprop-1-enyl )-1-(4-fluorophenyl)cyclopropane The method of Example 17 was repeated using acetyl chloride (0.46 ml), 1-(2-fluoro-3-hydroxyprop-1-enyl)-1-(4-fluorophenyl)cyclopropane (Example 12) (0.2 g), benzene (12 ml) and pyridine to yield the title compound (0.23 g, 96%).

EXAMPLE 21
1-(3-Acetoxy-2-fluoroprop-1-enyl)-1-(2-fluoro-4-trifluoromethylphenyl)cyclopropane The method of Example 17 was repeated using acetyl chloride (0.7 ml), 1-(2-fluoro-3-hydroxyprop-1-enyl)-1-(2-fluoro-4-trifluoromethylphenyl)cyclopropane (Example 13) (0.37 g), benzene (20 ml) and pyridine (0.12 ml) to yield the title compound (0.43 g, 99%).

EXAMPLE 22
1-(3-Acetoxy-2-fluoroprop-1-enyl)-1-(3,4-methylenedioxyphenyl)cyclopropane The method of Example 17 was repeated using acetyl chloride (1.4 ml), 1-(2-fluoro-3-hydroxyprop-1-enyl)-1-(3,4-methylenedioxyphenyl)cyclopropane (Example 14) (0.68 g), benzene (40 ml) and pyridine (0.26 ml) to yield the title compound (0.73 g, 93%).

EXAMPLE 23
1-(3-Acetoxy-2-fluoroprop-1-enyl)-1-(2,4-difluorophenyl)cyclopropane The method of Example 17 was repeated using acetyl chloride (0.46 ml), 1-(2,4-difluorophenyl)-1-(2-fluoro-3-hydroxyprop-1-enyl)cyclopropane (Example 15) (0.21 g), benzene (12 ml) and pyridine (0.09 ml) to yield the title compound (0.22 g, 92%).

EXAMPLE 24
1-(3-Acetoxy-2-fluoroprop-1-enyl)-1-(4-difluoromethoxyphenyl)cyclopropane The method of Example 17 was repeated using acetyl chloride (0.92 ml), 1-(4-difluoromethoxyphenyl)-1-(2-fluoro-3-hydroxyprop-1-enyl)cyclopropane Example 16) (0.49 g), benzene (24 ml) and pyridine (0.2 ml) to yield the title compound (0.55 g, 99%).

EXAMPLE 25
1-(4-Chlorophenyl)-1-(2-fluoro-3-(3-phenoxyphenyl)prop-1-enyl)cyclopropane A Grignard reagent, prepared from 3-phenoxyphenyl bromide (0.33 g) in dry tetrahydrofuran (2 ml) and magnesium (30 mg) under nitrogen using iodine as an initiator at ca 40 C for 50 min, was cooled to room temperature then treated with cuprous bromide (ca 20 mg) for 10 min. After cooling to −78° C., a solution of 1-(3-acetoxy-2-fluoroprop-1-enyl)-1-(4-chlorophenyl)cyclopropane (Example 17) (0.32 g) in tetrahydrofuran was added slowly with stirring, then the mixture was allowed to warm to room temperature overnight. The mixture was treated with water (4 ml), then extracted with diethyl ether (3×20 ml). The combined organic extracts were washed with water (2×10 ml), dried, and evaporated under reduced pressure. The residue was purified by preparative thin layer chromatography (solvent: diethyl ether/hexane; 1:9) and then preparative high performance liquid chromatography (column: C18; solvent: methanol; flow rate: 8 ml/min) to afford 1-(4-chlorophenyl)-1-(2-fluoro-3-(3-phenoxyphenyl)prop-1-enyl)cyclopropane (98 mg, 22%).

$^{13}$C NMR spectrum:
143.6(1), 128.2$^a$, 128.5$^a$, 131.4, −, −, 20.6(2), 16.0(3), 111.6(10), 159.7(261), 38.6(28), 138.2, 117.2, 157.4$^b$, 119.1, 129.8, 123.6, 157.0$^b$, 118.9, 129.8, 123.3.

EXAMPLE 26
1-(4-Ethoxyphenyl)-1-(2-fluoro-3-(3-phenoxyphenyl)prop-1-enyl)cyclopropane The method of Example 25 was repeated using a Grignard reagent, prepared from 3-phenoxyphenyl bromide (2.35 g), tetrahydrofuran (10 ml) and magnesium (0.21 g) and 1-(3-acetoxy-2-fluoroprop-1-enyl)-1-(4-ethoxyphenyl)cyclopropane (Example 18) (0.6 g). The residue after evaporation was purified by column chromatography (solvent: diethyl ether/hexane; 5:95) to afford 1-(4-ethoxy-phenyl)-1-(2-fluoro-3-(3-phenoxyphenyl)prop-1-enyl)cyclopropane (0.34 g, 41%)

$^{13}$C NMR spectrum:
137.2, 128.4, 114.2, 157.1$^a$, −, −, 20.6(2), 15.7(4), 111.5(10), 158.9(260), 38.7(28), 138.5, 117.1, 157.1$^a$, 119.1, 129.8, 123.6, 157.4$^a$, 118.9, 129.7, 123.3 and 63.4, 14.9 (OCH$_2$CH$_3$).

EXAMPLE27
1-(2-Fluoro-3-(3-phenoxyphenyl)prop-1-enyl)-1-(4-trifluoromethoxy-phenyl)cyclopropane The method of Example 25 was repeated using a Grignard reagent, prepared from 3-phenoxyphenyl bromide (0.16 g), tetrahydrofuran (2 ml) and magnesium (17 mg) and 1-(3-acetoxy-2-fluoroprop-1-enyl)-1-(4-trifluoromethoxyphenyl)cyclopropane (Example 19) (0.128 g). The residue after evaporation was purified by preparative thin layer chromatography (solvent: diethyl ether/hexane; 1:9) and then preparative high performance liquid chromatography (column: C8; solvent: methanol; flow rate: 3 ml/min) to afford 1-(2-fluoro-3-(3-phenoxyphenyl)prop-1-enyl)-1-(4-trifluoromethoxyphenyl) cyclopropane (46 mg, 25%).

$^{13}$C NMR spectrum:
138.2, 128.4, 120.7, 158.7, −, −, 20.6(2), 16.4(3), 110.5(11), 158.8(261) 38.6(28), 138.2, 117.3, 157.0$^a$, 119.1, 129.8, 123.6, 157.4$^a$, 118.9, 129.8, 123.4 and N (OCF$_3$).

EXAMPLE 28
1-(2-Fluoro-3-(3-phenoxyphenyl)prop-1-enyl)-1-(4-fluorophenyl)cyclopropane The method of Example 25 was repeated using a Grignard reagent, prepared from 3-phenoxyphenyl bromide (0.38 g), tetrahydrofuran (2 ml) and magnesium (28 mg) and 1-(3-acetoxy-2-fluoroprop-1-enyl)-1-(4-fluorophenyl)cyclopropane (Example 20) (0.12 g). The residue after evaporation was purified by preparative thin layer chromatography (solvent: diethyl ether/hexane; 1:9) and then preparative high performance liquid chromatography (column: phenyl; solvent: methanol; flow rate: 2 ml/min) to afford 1-(2-fluoro-3-(3-phenoxyphenyl)prop-1-enyl)-1-(4-fluorophenyl)cyclopropane (48 mg, 27%).
$^{13}$C NMR spectrum:
129.8(4), 128.9(8), 114.9(2), N, –, –, 20.6(2), 16.0(2), 111.1(10), 159.8(261), 38.6(28), 138.3, 117.2, 157.9$^a$, 119.1, 129.8, 123.6, 157.4$^a$, 118.9, 129.8, 123.3.

EXAMPLE 29
1-(2-Fluoro-3-(3-phenoxyphenyl)prop-1-enyl)-1-(2-fluoro-4-trifluoromethylphenyl) cyclopropane The method of Example 25 was repeated using a Grignard reagent, prepared from 3-phenoxyphenyl bromide (0.26 g), tetrahydrofuran (2 ml) and magnesium (22 mg) and 1-(3-acetoxy-2-fluoroprop-1-enyl)-1-(2-fluoro-4-trifluoromethylphenyl)cyclopropane (Example 21) (0.1 g). The residue after evaporation was purified by preparative thin layer chromatography (solvent: diethyl ether/hexane; 1:9) and then preparative high performance liquid chromatography (column: C8; solvent: methanol; flow rate: 2 ml/min) to afford 1-(2-fluoro-3-(3-phenoxyphenyl) prop-1-enyl)-1-(2-fluoro-4-trifluoromethylphenyl)cyclopropane (38 mg, 27%).
$^{13}$C NMR spectrum:
135.9(15), 161.8(250), 112.7(4.25), 130.4(8.33), 120.7(4), 131.5(4), 17.5, 14.2, 110.1(10), 159.6(250), 38.5(28), 138.1, 117.2, 157.0$^a$, 119.1, 129.7, 123.6, 157.4$^a$, 118.9, 129.8, 123.3 and 123.4 (272.3) (CF$_3$).

EXAMPLE 30
1-(2-Fluoro-3-(3-phenoxyphenyl)prop-1-enyl)-1-(3,4-methylenedioxyphenyl)cyclopropane The method of Example 25 was repeated using a Grignard reagent, prepared from 3-phenoxyphenyl bromide (0.40 g), tetrahydrofuran (2 ml) and magnesium (30 mg) and 1-(3-acetoxy-2-fluoroprop-1-enyl)-1-(3,4-methylenedioxyphenyl)cyclopropane (Example 22) (0.32 g). The residue after evaporation was purified by preparative thin layer chromatography (solvent: diethyl ether/hexane; 5:95) to afford 1-(2-fluoro-3-(3-phenoxyphenyl)prop-1-enyl)-1-(3,4-methylenedioxyphenyl)cyclopropane (82 mg, 19%).
$^{13}$C NMR spectrum:
139.2, 108.4$^a$, 145.6$^b$, 147.4$^b$, 107.9$^a$, 120.5, 21.2(2), 15.8 (3), 111.4(10), 159.0(260), 38.7(28), 138.4, 117.1, 157.0$^C$, 119.1, 129.8, 123.6, 157.4$^c$, 119.0, 129.7, 123.3 and 100.8 (CH$_2$O$_2$).

EXAMPLE 31
1-(2,4-Difluorophenyl)-1-(2-fluoro-3-(3-phenoxyphenyl)prop-1-enyl)cyclopropane The method of Example 25 was repeated using a Grignard reagent, prepared from 3-phenoxyphenyl bromide (0.28 g), tetrahydrofuran (2 ml), magnesium (22 mg) and 1-(3-acetoxy-2-fluoroprop-1-enyl)-1-(2,4-difluorophenyl) cyclopropane (Example 23) (0.1 g). The residue after evaporation was purified by preparative thin layer chromatography (solvent: diethyl ether/hexane; 1:9) and then preparative high performance liquid chromatography (column: C8; solvent: methanol; flow rate: 2 ml/min) to afford 1-(2,4-difluorophenyl)-1-(2-fluoro-3-(3-phenoxyphenyl)prop-1-enyl)cyclopropane (80 mg, 56%).
$^{13}$C NMR spectrum:
N, N, 103.6(26,26), N, 110.6(21,3), 131.5(10,6), 17.1, 14.1, 110.8(9), 158.9(260), 38.5(28), 138.3, 117.1, 157.0$^a$, 119.1, 129.8, 123.6, 157.4$^a$, 118.9, 129.7, 123.3.

EXAMPLE 32
1-(4-Difluoromethoxyphenyl)-1-(2-fluoro-3-(3-phenoxyphenyl)prop-1-enyl)cyclopropane The method of Example 25 was repeated using a Grignard reagent, prepared from 3-phenoxyphenyl bromide (0.28 g), tetrahydrofuran (2 ml) and magnesium (24 mg) and 1-(3-acetoxy-2-fluoroprop-1-enyl)-1-(4-difluoromethoxyphenyl)cyclopropane (Example 24) (94 mg). The residue after evaporation was purified by preparative thin layer chromatography (solvent: diethyl ether/hexane; 1:9) and then preparative high performance liquid chromatography (column: C18; solvent: methanol; flow rate: 8 ml/min) to afford 1-(4-difluoromethoxyphenyl)-1-(2-fluoro-3-(3-phenoxyphenyl)prop-1-enyl)cyclopropane (30 mg, 23%).
$^{13}$C NMR spectrum:
142.4, 128.6, 119.3, ca 149, –, –, 20.6, 16.2(3), 110.8(11), ca 159, 38.6(28), 138.2, 117.2, 177.0$^a$, 119.1, 129.8, 123.6, 157.4$^a$, 118.9, 129.8, 123.3 and 116.1(259) (OCHF$_2$).

EXAMPLE 33
1-(4-Chlorophenyl)-1-(2-fluoro-3-(4-fluoro-3-phenoxyphenyl)prop-1-enyl)cyclopropane The method of Example 25 was repeated using a Grignard reagent, prepared from 4-fluoro-3-phenoxyphenyl bromide (0.5 g), tetrahydrofuran (2 ml) and magnesium (38.6 mg) and 1-(3-acetoxy-2-fluoroprop-1-enyl)-1-(4-chlorophenyl) cyclopropane (Example 17) (0.34 g). The residue after evaporation was purified by preparative thin layer chromatography (solvent: diethyl ether/hexane; 1:9) and then preparative high performance liquid chromatography (column: Nitrile; solvent: methanol; flow rate: 2 ml/min) to afford 1-(4-chlorophenyl)-1-(2-fluoro-3-(4-fluoro-3-phenoxyphenyl)prop-1-enyl)cyclopropane (0.11 mg, 23%).
$^{13}$C NMR spectrum:
143.5(1), 128.3$^a$, 128.6$^a$, 131.5, –, –, 20.6(2), 16.2(3), 110.8, 159.4(261), 38.1(28), 133.2(3), 121.9, 143.6(11), 153.2 (248), 117.0(18), 124.8(7), N, 117.2, 129.8, 123.3.

EXAMPLE 34
1-(4-Ethoxyphenyl)-1-(2-fluoro-3-(4-fluoro-3-phenoxyphenyl)prop-1-enyl)cyclopropane The method of Example 25 was repeated using a Grignard reagent, prepared from 4-fluoro-3-phenoxyphenyl bromide (0.246 g), tetrahydrofuran (2 ml) and magnesium (21 mg) and 1-(3-acetoxy-2-fluoroprop-1-enyl)-1-(4-ethoxyphenyl) cyclopropane (Example 18) (0.176 g). The residue after evaporation was purified by preparative thin layer chromatography (solvent: diethyl ether/hexane; 1:9) and then preparative high performance liquid chromatography (column: C18; solvent: methanol; flow rate: 8 ml/min) to afford 1-(4-ethoxyphenyl)-1-(2-fluoro-3-(4-fluoro-3-phenoxyphenyl)-prop-1-enyl)cyclopropane (32 mg, 12%).
$^{13}$C NMR spectrum:
137.0, 128.4, 114.1, 157.1$^a$, –, –, 20.6(2), 15.6(3), 111.7(10), 158.6(260), 38.3(28), 133.4(3), 121.9, 143.5(12), ca 153, 117.0(18), 124.8(6), 157.4$^a$, 117.3, 129.7, 123.2 and 63.4, 14.9 (OCH$_2$CH$_3$).

EXAMPLE 35
1-(2-Fluoro-3-(4-fluoro-3-phenoxyphenyl)prop-1-enyl)-1-(4-fluorophenyl)cyclopropane The method of Example 25 was repeated using a Grignard reagent, prepared from 4-fluoro-3-phenoxyphenyl bromide (0.3 g), tetrahydrofuran (2 ml) and magnesium (21 mg) and 1-(3-acetoxy-2-fluoroprop-1-enyl)-1-(4-fluorophenyl)-cyclopropane (Example 20) (88 mg). The residue after evaporation was purified by preparative thin layer chromatography (solvent: diethyl ether/hexane; 1:9) and then preparative high performance liquid chromatography (column: C18; solvent: methanol; flow rate: 2 ml/min) to afford 1-(2-fluoro-3-(4-fluoro-3-phenoxy-phenyl)prop-1-enyl)-1-(4-fluorophenyl)cyclopropane (45.6 mg, 37%).

EXAMPLE 36

1-(2-Fluoro-3-(4-fluoro-3-phenoxyphenyl)prop-1-enyl)-1-(2-fluoro-4-trifluoromethylphenyl)cyclopropane The method of Example 25 was updated using a Grignard reagent, prepared from 4-fluoro-3-phenoxyphenyl bromide (0.26 g), tetrahydrofuran (2 ml) and magnesium (22 mg) and 1-(3-acetoxy-2-fluoroprop-1-enyl)-1-(2-fluoro-4-trifluoromethylphenyl)cyclopropane (Example 21) (0.1 g). The residue after evaporation was purified by preparative thin layer chromatography (solvent: diethyl ether/hexane; 1:9) and then preparative high performance liquid chromatography (column: phenyl; solvent: methanol; flow rate: 2 ml/min) to afford 1-(2-fluoro-3-(4-fluoro-3-phenoxyphenyl)prop-1-enyl)-1-(2-fluoro-4-trifluoromethylphenyl)cyclopropane (38 mg, 27%).

$^{13}$C NMR spectrum:

N, 161.8(250), 112.7(4,25), N, 120.7(4), 131.4(4), 17.5, 14.2, 110.2(10), 159.3(261), 38.0(28), 132.8(4), 121.9, ca 143, 153.2(248), 117.0(18), 124.8(7), 157.2, 117.3, 129.7, 123.2 and N ($CF_3$).

EXAMPLE 37

1-(2-Fluoro-3-(4-fluoro-3-phenoxyphenyl)prop-1-enyl)-1-(3,4-methylenedioxyphenyl)cyclopropane The method of Example 25 was repeated using a Grignard reagent, prepared from 4-fluoro-3-phenoxyphenyl bromide (0.313 g), tetrahydrofuran. (2 ml) and magnesium (24 mg) and 1-(3-acetoxy-2-fluoroprop-1-enyl)-1-(3,4-methylenedioxyphenyl) cyclopropane (Example 22) (0.138 g). The residue after evaporation was purified by preparative thin layer chromatography (solvent: diethyl ether/hexane; 1:9) to afford 1-(2-fluoro-3-(4-fluoro-3-phenoxyphenyl)prop-1-enyl)-1-(3,4-methylenedioxyphenyl)cyclopropane (52 mg, 26%).

$^{13}$C NMR spectrum:

139.1, 108.3$^a$, 145.7$^b$, 147.4$^b$, 107.9$^a$, 120.5, 21.3(2), 15.7 (3) 111.6(10), 158.7(261), 38.1(28), 133.2(3), 121.9, 143.6(11), 153.2(248), 117.0(18), 124.8(6), 157.2, 117.3, 129.7, 123.2 and 100.8 ($CH_2O_2$).

EXAMPLE 38

1-(2,4-Difluorophenyl)-1-(2-fluoro-3-(4-fluoro-3-phenoxyphenyl)-prop-1-enyl)cyclopropane The method of Example 25 was repeated using a Grignard reagent, prepared from 4-fluoro-3-phenoxyphenyl bromide (0.31 g), tetrahydrofuran (2 ml) and magnesium (22 mg) and 1-(3-acetoxy-2-fluoroprop-1-enyl)-1-(2,4-difluorophenyl) cyclopropane (Example 23) (0.11 g). The residue after evaporation was purified by preparative thin layer chromatography (solvent: diethyl ether/hexane; 1:9) and then preparative high performance liquid chromatography (column: C18; solvent: methanol; flow rate: 8 ml/min) to afford 1-(2,4-difluorophenyl)-3-(4-fluoro-3-phenoxyphenyl)prop-1-enyl)-1-(3,4-methylenedioxyphenyl)-cyclopropane (40 mg, 28%).

$^{13}$C NMR spectrum:

N, N, 103.6(26,26), N, 110.6(4,20), 131.5(6,9), 17.1, 14.1, 111.0(9), 158.6(259), 38.0(29), 133.1(5), 121.9, ca 143, 153.2(248), 117.0(19), 124.8(7), 157.2, 117.3, 129.7, 123.2.

EXAMPLE 39

1-(4-Difluoromethoxyphenyl)-1-(2-fluoro-3-(4-fluoro-3-phenoxyphenyl)prop-1-enyl)cyclopropane The method of Example 25 was repeated using a Grignard reagent, prepared from 4-fluoro-3-phenoxyphenyl bromide (0.31 g), tetrahydrofuran (2 ml) and magnesium (20 mg) and 1-(3-acetoxy-2-fluoroprop-1-enyl)-1-(4-difluoromethoxyphenyl)cyclopropane (Example 24) (0.155 g). The residue after evaporation was purified by preparative thin layer chromatography (solvent: diethyl ether/hexane; 1:9) and then preparative high performance liquid chromatography (column: C18; solvent: methanol; flow rate: 8 ml/min) to afford 1-(4-difluoromethoxyphenyl)-3-(4-fluoro-3-phenoxyphenyl)prop-1-enyl)-1-(3,4-methylenedioxyphenyl)cyclopropane (120 mg, 54%).

$^{13}$C NMR spectrum:

142.3, 128.6, 119.3, 149.2(3), –, –, 20.6(3), 16.1(3), 111.0 (9), 158.8(261), 38.1(29), 133.1(3), 121.9, 143.7(11), 153.2(247), 117.0(18), 124.9(6), 157.2, 117.3, 129.7, 123.3 and 116.0(259) ($OCHF_2$).

EXAMPLE 40

1-(2-Fluoro-3-(4-fluoro-3-phenoxyphenyl)prop-1-enyl)-1-(4-trifluoromethoxyphenyl)cyclopropane The method of Example 25 was repeated using a Grignard reagent, prepared from 4-fluoro-3-phenoxyphenyl bromide (0.27 g), tetrahydrofuran (2 ml) and magnesium (21 mg) and 1-(3-acetoxy-2-fluoroprop-1-enyl)-1-(4-trifluoromethoxyphenyl) cyclopropane (Example 19) (0.1 g). The residue after evaporation was purified by preparative thin layer chromatography (solvent: diethyl ether/hexane; 1:9) and then preparative high performance liquid chromatography (column: C18; solvent: methanol; flow rate: 3 ml/min) to afford 1-(2-fluoro-3-(4-fluoro-3-phenoxy-phenyl)prop-1-enyl)-1-(4-trifluoromethoxy phenyl) cyclopropane (29.4 mg, 21%).

$^{13}$C NMR spectrum:

N, 128.4, 120.7, 157.7, –, –, 20.6(3), 16.3(3), 110.6(10), 159.5(261), 38.1(28), 133.1(8), 121.9, N, 152.9(248), 117.1(18), 124.8(6), 157.2, 117.4, 129.8, 123.3 and N ($OCF_3$).

EXAMPLE 41 Bioassay

Residual soil activity of the compounds of Examples 25 to 40 was assessed against cornroot worm (*Diabrotica balteata*) using the following technique.

A known quantity of test compound dissolved in 1.0 ml acetone was applied evenly to a standard amount (22 g) of a sandy soil with a 10% moisture content. After 1 hour, 10 larvae were introduced. The temperature was maintained at 20° C. ±1° C. and mortality assessed after 48 hours. Two replicates of 10 larvae were used at each of 5 dose levels per compound. $LC_{50}$ values were calculated as concentration of insecticide in the standard amount of soil using probit analysis.

For comparison purposes, the activity results are also given for the following compounds prepared in accordance with the methods described in UK Patent No. 2167749 and lacking a fluorine atom adjacent the double bond:

1-(4-chlorophenyl)-1-(E-3-(4-fluoro-3-phenoxyphenyl) prop-1-enyl)-cyclopropane—"Comp. A"

1-(4-ethoxyphenyl)-1-(E-3-(4-fluoro-3-phenoxyphenyl) prop-1-enyl)-cyclopropane—"Comp. B"

1-(4-fluorophenyl)-1-(E-3-(4-fluoro-3-phenoxyphenyl) prop-1-enyl)-cyclopropane—"Comp. C"

1-(4-trifluoromethylphenyl)-1-(E-3-(3-phenoxyphenyl) prop-1-enyl)-cyclopropane—"Comp. D"

The results are given in Table 1 below.

TABLE 1

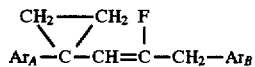 (III)

| Example | X | Y | Z | Residual Soil Activity (LC$_{50}$) (ppm) |
|---|---|---|---|---|
| 25 | 4-Cl | H | F | 0.031 |
| 26 | 4-OEt | H | F | 0.029 |
| 27 | 4-OCF$_3$ | H | F | 0.038 |
| 28 | 4-F | H | F | 0.015 |
| 29 | 2-F,4-CF$_3$ | H | F | 0.030 |
| 30 | 3,4-CH$_2$O$_2$ | H | F | 0.021 |
| 31 | 2,4-diF | H | F | — |
| 32 | 4-OCHF$_2$ | H | F | 0.055 |
| 33 | 4-Cl | F | F | — |
| 34 | 4-OEt | F | F | 0.031 |
| 35 | 4-F | F | F | 0.032 |
| 36 | 2,F,4-CF$_3$ | F | F | 0.021 |
| 37 | 3,4-CH$_2$O$_2$ | F | F | 0.055 |
| 39 | 4-OCHF$_2$ | F | F | 0.033 |
| Comp A | 4-Cl | F | H | 0.68 |
| Comp B | 4-OEt | F | H | 0.43 |
| Comp C | 4-F | F | H | 0.059 |
| Comp D | 4-OCF$_3$ | H | H | 0.059 |

The refractive indices (n$_D$) of the compounds of Examples 25, 26, 28–31, 33–39 are respectively 1.5910, 1.5922, 1.6300, 1.5922, 1.5835, 1.6093, 1.6041, 1.6008, 1.5985, 1.5735, 1.5768, 1.6058 and 1.5692.

Formulation of Insecticidal Compositions

General methods of preparing soil insecticidal compositions have been described hereinbefore. Although liquid compositions containing the active ingredient may be applied to the soil, solid compositions are more usually employed for the purposes of this invention. These are preferably formulated as granules in which the active compound is supported on a mineral support, e.g. granules or attapulgite, pumice or gypsum, or granules of vegetable matter e.g. those derived from corn cobs. They may be applied to soil at rates of 5 to 25 kg/ha, and preferably at 5 to 15 kg/ha. The granules may contain from 0.25 to 5.0% and preferably 0.5 to 2.5% by weight of the active ingredient, and the stability of the granules may be improved and the rate of release of the active ingredient may be regulated by the incorporation of a resin e.g., wood rosin or by coating with a polymeric substance e.g., a polyvinyl alcohol based material. The formulated granules may be obtained by spraying the granular support with a solution of the active ingredient in a volatile solvent and, after absorption into the granules, drying the granules to volatilise the solvent.

For example, a solution of the active ingredient (20 g) and wood rosin (50 g) in methylene chloride (200 ml) is sprayed on gypsum granules (193 g) available commercially under the Trade Mark Agsorb-S, grade 2100G. The granules are then dried in a rotary drum mixer to produce granules containing 1% active ingredient.

The granules may be applied to the surface of the soil adjacent to the furrow in which the plants are growing, and may be lightly incorporated in the soil thereafter, or the granules may be placed in the furrows with the seed at the time of planting.

Alternative methods of applying the compounds include coating seeds by fluid bed polymer coating techniques e.g. polyurea micro-encapsulation.

We claim:

1. A soil pesticide compound of formula I:

$$Ar_A-C(-CH_2CH_2-)-CH=C(F)-CH_2-Ar_B \quad (I)$$

in which formula:

Ar$_A$ represents a phenyl or naphthyl group optionally substituted by one or more groups selected from halogen, alkoxy, haloalkoxy, methylenedioxy, C$_1$-C$_6$ alkyl and C$_1$-C$_6$ haloalkyl; and Ar$_B$ represents a phenyl group substituted by a phenoxy, phenyl, benzyl or benzoyl group and is optionally further substituted;

the configuration of the aryl cyclopropyl group and the group CH$_2$Ar$_B$ about the double bond being mutually trans.

2. A compound according to claim 1 wherein Ar$_A$ is a substituted phenyl group.

3. A compound according to claim 2 wherein the phenyl group is substituted at the 3-(meta) and/or 4-(para) position by fluorine, bromine, chlorine, a C$_1$-C$_6$ alkyl group, a C$_1$-C$_6$ haloalkoxy group comprising one or more halogens or a C$_1$-C$_6$ haloalkyl group.

4. A compound according to claim 1 wherein Ar$_B$ is a phenyl group substituted at the 3-(meta) position by phenoxy, phenyl, benzyl or benzoyl and optionally further substituted by fluorine at the 4-(para) position.

5. A process for the preparation of a pesticidal compound of formula I according to claim 1 comprising the catalytic reaction of a nucleophilic species formally of formula Ar$_B$— with a compound of formula

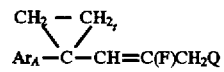

where Q represents a good leaving group.

6. A process according to claim 5 wherein the nucleophilic species is present in the form of a Grignard reagent.

7. An Insecticidal composition comprising an insecticidally effective amount of a compound of formula I as defined in any one of claims 1 to 4 in association with an agriculturally acceptable diluent.

8. An insecticidal composition according to claim 7 suitable for use for combating soil borne insect pests.

9. An insecticidal composition according to claim 7 or 8 in the form of granules, a dust or an emulsifiable concentrate.

10. An insecticidal composition according to claim 9 in the form of granules.

11. An insecticidal composition according to claim 9 wherein the compound of formula I is present in an amount of from 0.5 to 5% by weight.

12. A method of combating soil borne insect pests comprising applying to the soil or as a seed treatment a composition according to any one of claims 7 to 11.

13. A method according to claim 12 wherein the rate of application to the locus of infestation is in the range of from 1 to 100 g active ingredient per hectare.

14. A process for preparation of a pesticidal compound of formula I according to claim 1 comprising the catalytic reaction of a nucleophilic species formally of formula Ar$_B$ with a compound of formula

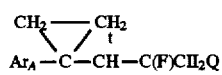

where Q represents a good leaving group, where a compound

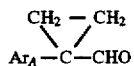

is reacted with an alkyl dichlorofluoroacetate to provide a compound

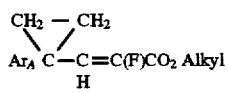

which is converted to the compound

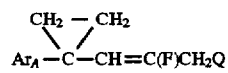

by converting the $CO_2$-Alkyl group to a group $CH_2$-Q.

15. A process as claimed in claim 14 wherein the $CO_2$-Alkyl group is converted to the compound

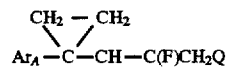

by reducing it with lithium aluminum hydrochloride to provide the corresponding alcohol.

* * * * *